United States Patent [19]

Maass

[11] 3,989,838

[45] Nov. 2, 1976

[54] URICOSURIC COMPOSITIONS AND METHOD OF PRODUCING URICOSURIA AND HYPOURICEMIA

[75] Inventor: Alfred R. Maass, Swarthmore, Pa.

[73] Assignee: SmithKline Corporation, Philadelphia, Pa.

[22] Filed: Sept. 22, 1975

[21] Appl. No.: 615,253

[52] U.S. Cl. .............................................. 424/275
[51] Int. Cl.$^2$ ...................................... A61K 31/38
[58] Field of Search ................................. 424/275

[56] References Cited
UNITED STATES PATENTS
3,758,506   9/1973   Godfroid et al. .................. 424/250

Primary Examiner—Stanley J. Friedman
Attorney, Agent, or Firm—Richard D. Foggio; William H. Edgerton

[57] ABSTRACT

Uricosuric compositions containing 2,3-dichloro-4-(α-hydroxy-2-thenyl)phenoxyacetic acid, its alkali metal salts or pharmaceutically acceptable base addition salts and methods of producing uricosuria and hypouricemia by administering said compounds. Either the racemic mixture or a separated d-or l-optical isomer may be employed as the active ingredient.

8 Claims, No Drawings

URICOSURIC COMPOSITIONS AND METHOD OF PRODUCING URICOSURIA AND HYPOURICEMIA

This invention relates to novel uricosuric compositions containing an active ingredient which increases urinary excretion and clearance of uric acid, and to a method of producing uricosuria and hypouricemia by administering nontoxic effective quantities of said ingredient to a subject in need thereof. More specifically, the active ingredient used in the compositions and methods of this invention is 2,3-dichloro-4-(α-hydroxy-2-thenyl)phenoxyacetic acid which has the following formula:

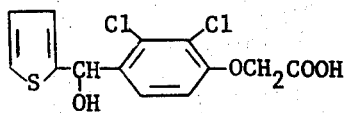

FORMULA I or an alkali metal salt of said acid, for example the sodium or potassium salt, or a pharmaceutically acceptable addition nontoxic salt of said acid formed with a base, for example the piperazine or (trihydroxymethyl)methylamine salt.

The compound of formula I, when present as a racemic mixture, can be resolved into $d$ or $l$ optical isomers by fractional crystallization of its salt with an optically active amine from appropriate solvents. Unless otherwise stated herein it is intended to include in the structural formulas and in the claims, both the racemic mixtures as well as the separated $d$ and $l$ isomers.

The racemic acid of formula I and its preparation is described in Eur. J. Med. Chem.—Chimica Therapeutica, 9(6):625-633 (1974). The racemate is also conveniently prepared from 2,3-dichloro-4-(2-thenoyl)phenoxyacetic acid (U.S. Pat. No. 3,758,506) by reduction with sodium borohydride. The compound of formula I is disclosed as having diuretic activity.

The utility of 2,3-dichloro-4-(α-hydroxy-2-thenyl)-phenoxyacetic acid and its salts as a diuretic is enhanced by its uricosuric and hypouricemic activity. Among the secondary effects of long term diuretic therapy, for example with the thiazide-type diuretics, furosemide and ethacrynic acid, there is often an increase in serum uric acid levels. Such an increase can cause crises of gouty arthritis. Therefore a diuretic with uricosuric and hypouricemic activity is of great value.

The uricosuric activity of 2,3-dichloro-1 4-(α-hydroxy-2-thenyl)phenoxyacetic acid or its salts is determined by intravenous administration of a test compound to the phosphate-mannitol infused mongrel dog as a rapid injection at doses of 5, 7.5 or 15 mg/kg. Renal clearance studies are compared against control experiments conducted in the same dogs. The urate clearance is calculated from the plasma and urinary concentrations. In this study, 2,3-dichloro-4-(α-hydroxy-2-thenyl)phenoxyacetic acid markedly increased the urinary excretion and clearance of uric acid. For example, racemic 2,3-dichloro-4-(α-hydroxy-2-thenyl)phenoxyacetic acid at a dose of 5 mg/kg i.v. increased urate excretion as a percentage of glomerular filtration rate from a value of 27% up to 40% and at a dose of 15 mg/kg i.v. increased it from 28% up to 74%. Both the separated $d$-and $l$-isomers produced comparable results at an i.v. dose of 7.5 mg/kg.

The uricosuric compositions of this invention are prepared in conventional dosage unit forms by incorporating 2,3-dichloro-4-(α-hydroxy-2-thenyl)phenoxyacetic acid or a pharmaceutically acceptable salt thereof, in a nontoxic amount sufficient to produce uricosuria and hypouricemia in a designated subject, with a nontoxic pharmaceutical carrier according to accepted procedures. Preferably the compositions will contain the active ingredient in an active but nontoxic amount selected from about 25 mg. to about 500 mg. of active ingredient per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

The method in accordance with this invention comprises administering internally to an animal subject in need of uricosuric and hypouricemic activity the compound 2,3-dichloro-4-(α-hydroxy-2-thenyl)phenoxyacetic acid or a salt thereof, usually combined with a pharmaceutical carrier, in a nontoxic amount sufficient to produce said activity. The active ingredient will be administered preferably in a dosage unit, in an active, nontoxic quantity selected from about 25 mg. to about 500 mg. of the parent chemical of formula I. The route of administration may be orally or parenterally, the oral route being preferred. Advantageously equal doses will be administered two to four times daily with the daily dosage regimen being from about 50 mg. to about 1000 mg. When the method described above is carried out uricosuria and hypouricemia is produced with a minimum of side effects.

The pharmaceutical preparations are made following the conventional techniques of the pharmaceutical chemist involving mixing, granulating and compressing when necessary, or variously mixing and dissolving the ingredients as appropriate to the desired end product. The following examples illustrate the preparation of the active ingredients employed herein and their incorporation into compositions of this invention.

EXAMPLE 1

Ethanol (300 ml.) is added to a suspension of 6.62 g. (0.02 mol) of 2,3-dichloro-4-(2-thenoyl)phenoxyacetic acid in 100 ml. of water and 16 ml. of 10% sodium hydroxide solution. To the resulting clear solution is added 1.14 g. (0.03 mol) of sodium borohydride and the mixture is stirred at room temperature for 5 hours. An additional 1.0 g. of sodium borohydride is added and the mixture is stirred at room temperature for 2 days. The reaction mixture is heated under reflux for 4 hours, concentrated under reduced pressure and acidified. The precipitate is crystallized from ethanol/water to give $d,l$-2,3-dichloro-4-($\alpha$-hydroxy-2-thenyl)phenoxyacetic acid, m.p. 141°–144° C.

EXAMPLE 2

To a suspension of 18.3 g. (0.055 mol) of racemic 2,3-dichloro-4-($\alpha$-hydroxy-2-thenyl)phenoxyacetic acid, prepared as in Example 1, in 20 ml. of ethanol is added a solution of 7.31 g. (0.061 mol) of 1-(−)-$\alpha$-methylbenzylamine in 5 ml. of ethanol. The mixture is heated on the steam bath until solution is completed, then diluted with sufficient ether to give a total volume of 1000 ml., giving a precipitate which is recrystallized from ethanol-ether three times to give crystals, m.p. 188°–189° C.

The crystalline salt with 1-(−)-$\alpha$-methylbenzylamine (9.1 g.) is suspended in 100 ml. of water and dilute hydrochloric acid is added to make acidic. The mixture is extracted with ether, the extract is dried and concentrated. As crystals begin to fall from the solution, excess petroleum ether is added and the mixture is cooled at −10° C. overnight. The crystals filtered are $d$-2,3-dichloro-4-($\alpha$-hydroxy-2-thenyl)phenoxyacetic acid, m.p. 119°–120° C., $[\alpha]_D^{25}$ (1, ethanol) = + 13.8°.

All the mother liquors from the above preparation are combined and concentrated in vacuo. The residue is suspended in water and the mixture is made acidic with 1N hydrochloric acid, then extracted with ether. The extract is dried and concentrated to leave 13.1 g. (0.0394 mol) of crystalline acid. The latter in 20 ml. of ethanol is treated with a solution of 5.3 g. (0.043 mol) of $d$-(+)-$\alpha$-methylbenzylamine in ethanol and the resulting solution is diluted to 1000 ml. with ether. Cooling precipitates the salt, m.p. 187°–189° C, after it is twice recrystallized from ethanol-ether.

This crystalline salt (8.3 g.) is suspended in 100 ml. of water and dilute hydrochloric acid is added to make acidic. The mixture is extracted with ether, the extract is dried and concentrated. When crystals being to fall from solution, excess petroleum ether is added and the mixture is cooled to −10° C. The crystals are filtered to give $l$-2,3-dichloro-4-($\alpha$-hydroxy-2-thenyl)phenoxyacetic acid, m.p. 121°–122° C. (dec.), $[\alpha]_D^{25}$ (1, ethanol) = −13.8°.

EXAMPLE 3

| Ingredients | Mg./Capsule |
| --- | --- |
| 2,3-Dichloro-4-($\alpha$-hydroxy-2-thenyl)phenoxyacetic acid | 250 |
| Magnesium stearate | 2 |
| Lactone | 100 |

The above ingredients are screened through a No. 40 mesh screen, mixed and filled into No. 0 hard gelatin capsules. The capsules are administered to a subject twice daily.

What is claimed is:

1. A method of producing uricosuria and hypouricemia which comprises administering internally to a subject in need thereof a nontoxic amount sufficient to produce uricosuria and hypouricemia of the compound 2,3-dichloro-4-($\alpha$-hydroxy-2-thenyl)phenoxyacetic acid or an alkali metal salt of said acid or a pharmaceutically acceptable addition salt of said acid formed with a base.

2. The method of claim 1 in which the active ingredient is administered with a pharmaceutical carrier in dosage unit form.

3. The method of claim 2 in which the administration is orally.

4. The method of claim 1 in which a daily dosage of from about 50 mg. to about 1000 mg. of active ingredient is administered.

5. The method of claim 2 in which dosage units containing from about 25 mg. to about 500 mg. of active ingredient are administered from 2 to 4 times daily.

6. The method of claim 1 in which the active ingredient is $d,l$-2,3-dichloro-4-($\alpha$-hydroxy-2-thenyl)-phenoxyacetic acid.

7. The method of claim 1 in which the active ingredient is $d$-2,3-dichloro-4-($\alpha$-hydroxy-2-thenyl)-phenoxyacetic acid.

8. The method of claim 1 in which the active ingredient is $l$-2,3-dichloro-4-($\alpha$-hydroxy-2-thenyl)phenoxyacetic acid.

* * * * *